United States Patent
Van Weelden et al.

(10) Patent No.: US 7,908,912 B2
(45) Date of Patent: Mar. 22, 2011

(54) OIL SENSING SYSTEM FOR AN INTERNAL COMBUSTION ENGINE

(75) Inventors: Curtis L. Van Weelden, Waukesha, WI (US); Dean S. Wardle, Waukesha, WI (US)

(73) Assignee: HUSCO Automotive Holdings LLC, Waukesha, WI (US)

( * ) Notice: Subject to any disclaimer, the term of this patent is extended or adjusted under 35 U.S.C. 154(b) by 328 days.

(21) Appl. No.: 12/120,575

(22) Filed: May 14, 2008

(65) Prior Publication Data

US 2008/0282786 A1 Nov. 20, 2008

Related U.S. Application Data

(60) Provisional application No. 60/938,328, filed on May 16, 2007.

(51) Int. Cl.
*G01M 15/00* (2006.01)
(52) U.S. Cl. .................................. 73/114.56
(58) Field of Classification Search ............. 73/114.55, 73/114.56

See application file for complete search history.

(56) References Cited

U.S. PATENT DOCUMENTS

| | | | | |
|---|---|---|---|---|
| 4,627,272 A | * | 12/1986 | Wright | 73/54.23 |
| 4,876,529 A | * | 10/1989 | Kubota et al. | 340/450.3 |
| 5,377,531 A | * | 1/1995 | Gomm | 73/53.05 |
| 7,677,086 B2 | * | 3/2010 | Albertson et al. | 73/54.02 |
| 2008/0093172 A1 | * | 4/2008 | Albertson et al. | 184/6.4 |
| 2008/0250851 A1 | * | 10/2008 | Keller et al. | 73/114.55 |
| 2009/0188755 A1 | * | 7/2009 | Staley et al. | 184/6.5 |
| 2010/0127718 A1 | * | 5/2010 | Albertson et al. | 324/694 |

* cited by examiner

*Primary Examiner* — Freddie Kirkland, III
(74) *Attorney, Agent, or Firm* — Quarles & Brady LLP; George E. Haas

(57) ABSTRACT

A system for detecting a characteristic of oil in a reservoir includes a sensor at least partially located in the reservoir. The sensor has a chamber for receiving oil from the reservoir, a detector member in the chamber, and an electromagnetic coil. Application of voltage across the electromagnetic coil moves the detector member and the presence and viscosity of oil in the chamber affects the rate of that movement. The electric current through the electromagnetic coil is measured and analyzed to determine an amount of time that the detector member took to move between two positions in the chamber. That amount of time is used to determine whether there is at least a predefined amount of oil in the reservoir and, if so, the viscosity of the oil.

24 Claims, 2 Drawing Sheets

OIL SENSING SYSTEM FOR AN INTERNAL COMBUSTION ENGINE

CROSS-REFERENCE TO RELATED APPLICATIONS

This application claims benefit of U.S. Provisional Patent Application No. 60/938,328 filed on May 16, 2007.

STATEMENT REGARDING FEDERALLY SPONSORED RESEARCH OR DEVELOPMENT

Not Applicable

BACKGROUND OF THE INVENTION

1. Field of the Invention

The present invention relates to apparatus for sensing oil in an internal combustion engine, and more particularly to such sensors that detect the level of oil in a reservoir of the engine and that provide a signal indicating the viscosity of the oil.

2. Description of the Related Art

Internal combustion engines are lubricated by oil that is stored in a reservoir, typically an oil pan located underneath the cylinder block of the engine. An oil pump draws the oil from the reservoir and forces it through passages to the top of the cylinder block. After exiting those passages, the oil lubricates various components of the engine, as it flows downward through the cylinder block by gravity ultimately returning into the reservoir.

A sensor often has been used to detect pressure at the outlet of the oil pump to provide an indication to the operator of the engine whether there is sufficient oil for proper lubrication. However, this pressure sensor does not provide an indication of the oil's viscosity. Engine lubricating oil is commercially available in different viscosities and a particular engine is designed to use a specific type of oil. If oil of an improper viscosity for a given engine is used, the components of that engine may not be properly lubricated and damage to those components may result.

Therefore, it is desirable to determine whether there is a sufficient amount of oil within the reservoir and whether that oil is the proper viscosity.

Operation of an engine usually is controlled by a microcomputer that monitors the level of engine usage and the operating conditions. From such monitoring the microcomputer is able to determine when the lubricating capability of the oil becomes depleted and the oil needs to be replaced. At that time the microcomputer provides an indication of that need to the engine operator. When the oil is changed, the service technician must manually reset that indication, a process that differs for each make of motor vehicle. Therefore, it is desirable to provide a mechanism by which the microcomputer can detect when the oil has been changed and automatically reset the oil change indication.

SUMMARY OF THE INVENTION

A sensor is provided to detect a characteristic of oil within a reservoir of an internal combustion engine. The sensor comprises a chamber for receiving oil from the reservoir, a ferromagnetic detector member movably received in the chamber, and an electromagnetic coil that produces a magnetic field. The detector member preferably is biased by a spring. Energizing the electromagnetic coil produces the magnetic field that moves the detector member in one direction through the chamber and deactivation of the electromagnetic coil terminates the magnetic field allowing the spring to drive the detector member in the opposite direction.

Oil from the reservoir enters the chamber within the sensor and affects the rate at which the detector member moves. Specifically, the absence of oil within the chamber, which then is filled with air, provides minimal resistance to the motion of the detector member. Because oil is more viscous than air, its presence within the sensor chamber provides a greater resistance to motion of the detector member. In fact, the amount of that resistance is a function of the viscosity of the oil, thus the rate at which the detector member moves is related to the viscosity of the fluid (air or oil) in the sensor chamber.

Movement of the ferromagnetic detector member with respect to the electromagnetic coil changes the permeance of the sensor's magnetic circuit which affects electric current flowing through that coil. By analyzing the waveform of that electric current, the relative speed of the detector member can be determined and then analyzed to determine whether oil is present within the sensor chamber and the viscosity of that oil. Specifically the amount of time that it takes the detector member to move between two positions in the chamber is measured from features of the electric current waveform. That amount of time is employed to determine the characteristic of the oil in the reservoir.

DETAILED DESCRIPTION OF THE INVENTION

Figure 1:
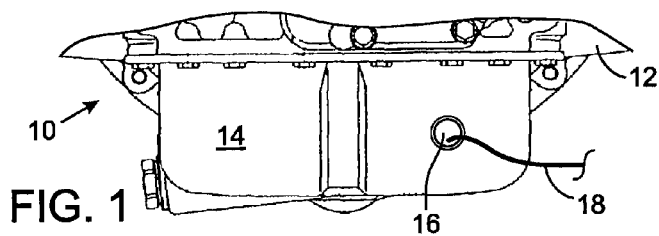
FIG. 1 is a side view of an oil pan on an internal combustion engine with a sensor according to the present invention mounted in a wall of the oil pan.

FIG. 1 illustrates an internal combustion engine 10 that has a cylinder block 12 at the bottom of which an oil pan 14 is attached. The oil pan 14 serves as a reservoir for lubricating oil used in the engine 10. An oil sensor 16 is located in an aperture on one side wall of the oil pan 14 at a position such that should the oil within the pan drop beneath the location of the sensor, there would be an undesirably small amount of oil in the reservoir. The sensor 16 is an electrically operated device that receives a signal via a cable 18.

Figure 2:
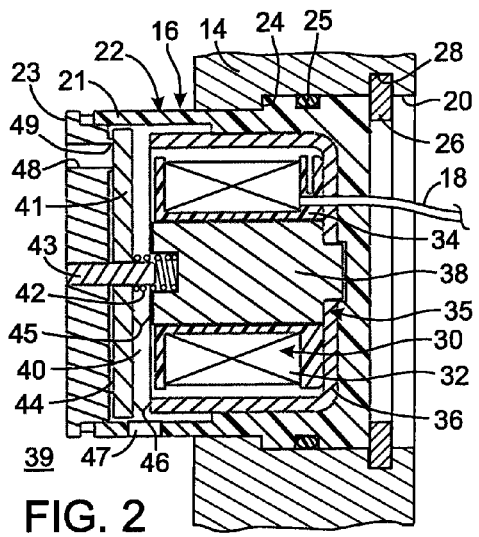
FIG. 2 is a cross sectional view through the sensor mounted on the oil pan.

With reference to FIG. 2, the oil sensor 16 is located within an aperture 20 in the oil pan 14 and has a housing 22 that engages a shoulder 24 in that aperture to limit how far the sensor can be inserted into the aperture. The housing 22 has a cup shaped piece 21 with an open end that is closed in a fluid tight manner by a disk 23. An O-ring 25 extends within a groove around the exterior of the sensor housing 22 to provide a fluid seal with respect to the oil pan 14. When the sensor housing 22 abuts the shoulder 24, a snap ring 26 is inserted in an annular groove 28 around the oil pan aperture 20 to secure the sensor in place.

The sensor housing 22 contains a solenoid 30 that has an electromagnetic coil 32 wound on a conventional plastic bobbin 34. The electromagnetic coil 32 and bobbin 34 are held within a magnetic core 35 formed by components of a ferromagnetic material, such as steel. Specifically the magnetic core 35 comprises a cup 36 and a cylindrical pole piece 38 located centrally within the cup and abutting the flat inside surface of the cup, thereby forming a core that has an E-shaped cross section. The interior of the cup 36 opens into a chamber 40 within the housing 22. A disc-shaped plate of ferromagnetic material forms a detector member 41 that is located within the chamber 40 and slides along a guide pin 43 that is embedded in a wall of the housing 22. The detector member 41 is biased away from the solenoid 30 by a coil spring 42. This biasing forms two working gaps 45 and 46 in the magnetic circuit between the core 35 and the detector member 41. One is an annular gap 46 around the lip of the cup 36 and the other gap 45 is at the exposed end of the cylindrical pole piece 38.

A first aperture 47 at the bottom of the sensor housing 22 provides a fluid drain passage between the sensor chamber 40 and the interior cavity 39 of the oil pan 14. The sensor housing 22 and the oil pan aperture 20 are keyed so that the sensor 16 only can be mounted on the oil pan 14 with the first aperture 47 facing downward, so that oil drains through that aperture by gravity. A second aperture 48 near the top of the sensor housing 22 provides another fluid passage between the sensor chamber 40 and the oil pan's interior cavity 39. The second aperture 48 extends through a boss 49 on an interior surface of the sensor chamber 40 against which the detector member 41 rests in the de-energized state of the solenoid 30, thereby closing the fluid passage provided by the second aperture. Two additional bosses 44 (only one being visible in FIG. 2) also are provided on that surface of the sensor chamber 40, so that the detector member 41 rests perpendicular to the axis of the guide pin 43.

The spring 42 normally biases the detector member 41 away from the solenoid 30 and its electromagnetic coil 32. When an electric voltage is applied to the solenoid, the electromagnetic 32 generates an magnetic field which attracts the detector member 41 toward the solenoid. The force of the magnetic field overcomes the force of the spring 42, thereby causing the detector member 41 to abut the open end of the cup 36 of the solenoid core 35. When the electric voltage is removed from the electromagnetic coil 32, the magnetic field ceases and the force of the spring 42 moves the detector member 41 away from the solenoid 30 returning that plate to the position illustrated in FIG. 2.

The speed at which the detector member 41 moves toward the solenoid 30, each time electric voltage is applied to the electromagnetic coil 32, is affected by the fluid within the chamber 40, and particularly the viscosity of that fluid. When there either is no oil within the oil pan 14, as occurs during an oil change, or the level of that oil is below the position of the sensor 16, any oil that was previously within the sensor chamber 40 drains out through the first aperture 47 and air enters that chamber. Air has a relatively low viscosity, as compared to conventional lubricating oils, thereby air in the chamber 40 allows more rapid motion of the detector member 41 in response to energizing the solenoid 30.

When the oil pan 14 is refilled with oil, the air in chamber 40 is trapped and prevents the oil from entering through the first aperture 47 at the bottom of the sensor housing 22. Note that in the de-energized state of the solenoid 30, the detector member 41 closes the second aperture 48 near the top of the housing. Thereafter, cycling the solenoid 30 on and off repeatedly moves the detector member 41 back and forth within the chamber 40, thereby intermittently opening the second aperture 48 to allow the air to escape and oil to enter through the first aperture 47. Typically the solenoid 30 is cycled at a frequency of one Hertz, for example, and five to seven cycles are adequate to exchange the fluid so that the chamber 40 becomes filled with oil. More or less cycles may be necessary depending on the operating frequency, the viscosity of the oil and the volume of the sensor chamber. When the chamber 40 contains oil, the greater viscosity of the oil, as compared to air, causes the detector member 41 to move slower.

Figure 3:
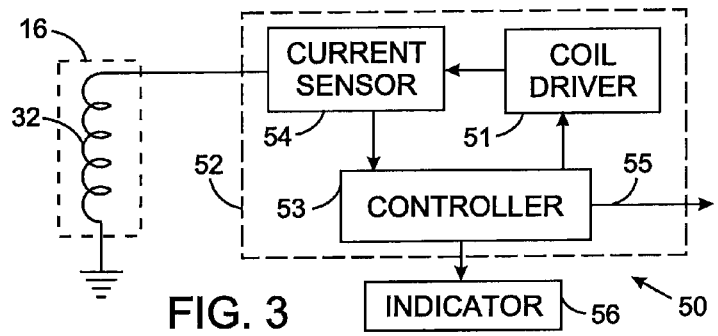
FIG. 3 is a block schematic diagram of a control circuit for operating the sensor and analyzing the electric current flowing through the sensor.

With reference to FIG. 3, the sensor 16, electrically represented by its electromagnetic coil 32, is part of an oil detecting system 50 and is connected to a control circuit 52. The control circuit 52 comprises a coil driver 51, a controller 53 and a current sensor 54. The electromagnetic coil 32 is energized by a fixed level of electric voltage produced by a coil driver 51 in response to a command from a controller 53 in the motor vehicle. The controller 53 may be a dedicated controller for the oil sensing or it may be one of the microcomputer based controllers already present for operating other components of the engine or the motor vehicle powered by the engine. The controller 53 executes a software program that is stored along with data in the controller's internal memory. That program activates the coil driver 51 to apply the fixed voltage across the electromagnetic coil 32. The resultant electric current flowing through the electromagnetic coil 32 is measured by a current sensor 54, which may be any of several well known types for sensing a direct current. The current sensor 54 provides an input signal to the controller 53 indicating the magnitude of the electric current flowing through the electromagnetic coil 32.

Figure 4:
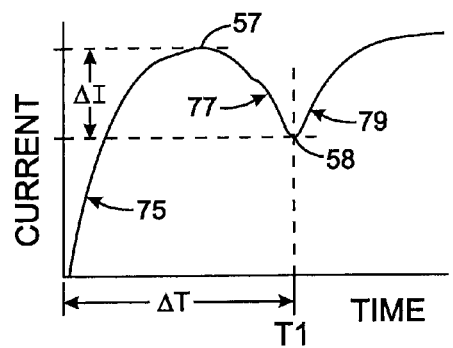
FIG. 4 is an exemplary waveform of the electric current flowing through the sensor.

With reference to the graph FIG. 4, when a drive voltage is initially applied to the electromagnetic coil 32, the resultant electric current begins to rise to a peak 57 and then drops precipitously to a cusp 58 at a time designated T1 when the detector member 41 strikes the solenoid core 35. The depth of the cusp, designated $\Delta I$, is a function of the velocity of the detector member and the changing magnetic permeance with the stroke of the solenoid. After the cusp 58 at time T1, the current rises again.

The controller 53 is able to detect when the input signal from the current sensor 54 indicates the occurrence of the cusp 58. The length of time $\Delta T$ between the initially applied electric current to the electromagnetic coil 32 and the cusp 58 varies depending upon the viscosity of the fluid within the sensor chamber 40. Therefore, by analyzing the current waveform, as provided by the signal from the current sensor 54, and particularly measuring the length of period $\Delta T$, the controller 53 is able to determine whether the chamber 40 is filled with air, indicating an abnormally low level of oil in the pan 14, or has oil therein, which denotes that the oil pan is adequately filled. The duration of period $\Delta T$ also varies as a function of the particular viscosity of the oil within the pan, i.e. the greater the viscosity, the longer the period $\Delta T$. Thus the controller 53 also is able to determine whether the oil within the pan has the proper viscosity for this particular engine. The controller 53 provides information about the oil level and viscosity via a communication link 55 to the instrument panel for the motor vehicle in which the engine 10 is located. The communication link 55 also can carry that information to other computers in the motor vehicle. As an alternative or an additional feature, the controller is connected to a separate indicator 56 through which the oil level and viscosity information are presented to a human operator.

Figure 5:
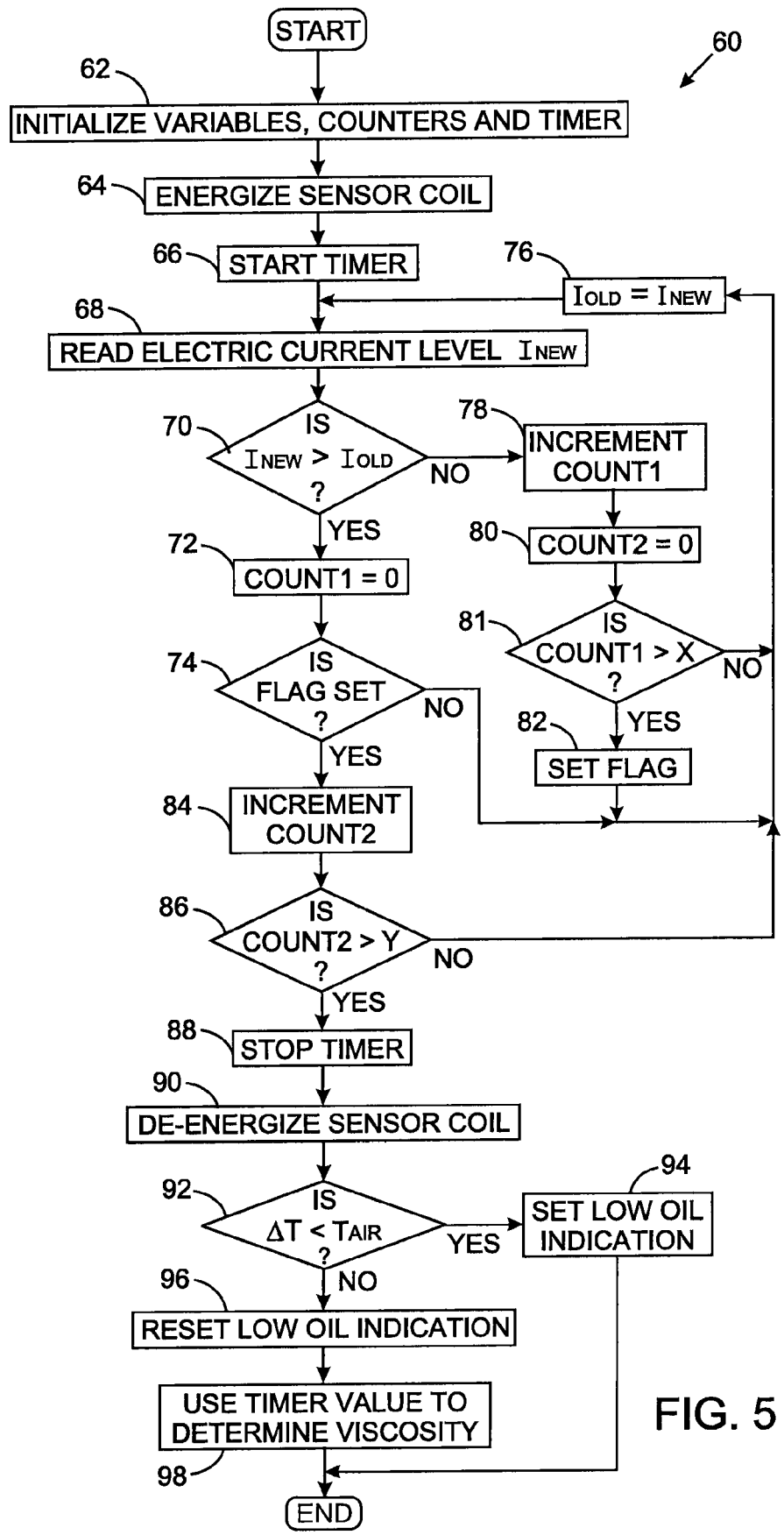
FIG. 5 is a flowchart of the process by which the control circuit determines the presence or absence of oil and the viscosity of any oil that is present.

To make those determinations the controller 53 performs a process 60 implemented by a software routine, such as the one depicted in FIG. 5. The process 60 commences at step 62 by the controller initializing the variables, counters and a timer used during the process. The coil driver 51 is signaled to apply a predefined, constant level of electric voltage to the valve's electromagnetic coil 32 at step 64. Next at step 66, the controller starts a software timer that measures how long it takes for the detector member 41 to travel from the position shown in FIG. 2 to the lip of the cup 36, at which time the cusp 58 occurs in the current waveform.

At step 68, the controller 53 reads the input signal from the current sensor 54 and determines the magnitude of the electric current ($I_{NEW}$) flowing through the electromagnetic coil 32 in the oil sensor 16. The present level of the electric current ($I_{NEW}$) is compared to the previous sensed level, designated $I_{OLD}$, which is stored temporarily in the controller's memory. When the oil sensor is initially activated, the current increases, i.e. presently sensed electric current level ($I_{NEW}$) is greater than the previously sensed electric current level ($I_{OLD}$). If that relationship exists, as determined at step 70, the process branches to step 72 at which the value (COUNT1) of a first counter stored in memory is reset to zero. Then a check is made whether a software flag is set. During the initial waveform segment 75, while the current level is increasing the counter remains a zero and the flag is not set. As a result, the process branches from step 74 to step 76 near the beginning of the process at which the value of $I_{OLD}$ is set equal to the most recently sensed electric current level. The cycle repeats by again reading the input signal from the current sensor 54 to obtain a new electric current measurement ($I_{NEW}$).

Eventually the coil current reaches a peak 57 (see FIG. 4) and begins decreasing during a subsequent waveform segment 77. During that waveform segment 77, the presently sensed electric current level ($I_{NEW}$) is less than the previously sensed electric current level ($I_{OLD}$), so that at step 70 the process now branches to a section the detects the downward portion of the current waveform after the peak 57. At step 78, the value (COUNT1) of a first software counter is incremented and the value COUNT2 of a second software counter is reset to zero at step 80. Then the first counter value COUNT1 is tested to determine if the count is greater than a threshold value X. Until that determination is true the process continues looping through steps 68, 70, 78-82 and 76. After X number of consecutive passes, COUNT1 is greater than X and the process branches from step 81 to step 82 where the flag is set.

If while the current was initially increasing waveform segment 75 (FIG. 4), a sporadic new current level measurement was less that the previous current level ($I_{NEW}$<$I_{OLD}$), this anomaly also causes the process to branch from step 70 to step 78 even though the current peak 57 has not occurred. As a result the first counter's value (COUNT1) is incremented during the anomaly, however due to the short duration of that anomaly, the COUNT1 never reaches a value of X and the flag does not get set at step 82. Thus when the current begins to increase again, i.e., $I_{NEW}$>$I_{OLD}$, in waveform segment 75 and the process advances once more from step 70 to step 74 the flag will not be found set and the process returns back through step 76 to obtain a new electric current measurement at step 68, just as though the anomaly never occurred.

In due course during waveform segment 77 after the current peak 57, the more than X consecutive electric current samples $I_{NEW}$ will be acquired that are less than the previously sensed electric current level ($I_{OLD}$), so that repeated branching through steps 78 and 80 results in the flag being set at step 82. Setting the flag indicates that the electric current waveform has reached the peak 57 and begun the downward waveform segment 77 toward the cusp 58. Until that cusp occurs the process continues to loop through steps 68, 70, 78-82 and 76.

Occurrence of the cusp 58, causes the coil current to again begin increasing in another waveform segment 79. The next time thereafter that step 70 is executed the process branches through step 72 to step 74. Now the controller 53 finds that the flag has been set which causes further advancement to step 84. A transient increase in the current level that may occur between the current peak 57 the cusp 58 is prevented from erroneously being considered as the cusp, by requiring that the current level remain increasing for a plurality (Y) of consecutive processing cycles. That requirement is implemented by incrementing the value COUNT2 of the second software counter on each pass through this processing branch and determining that the cusp 58 occurred only after the COUNT2 is greater than Y. Note that after a transient increase in the current level lasting less than Y consecutive processing cycles, the process again branches from step 70 through step 78 to step 80 at which the value COUNT2 of the second counter is reset to zero.

When the coil current level now increases for more than Y consecutive processing cycles as occurs during waveform segment 79, a determination is made that the cusp 58 occurred and the process branches to step 88. At this juncture, the controller 53 stops the timer and at step 90 signals the coil driver 51 to terminate applying the voltage to the sensor's electromagnetic coil 32.

The operation of the controller 53 enters a phase in which the timer value is analyzed to ascertain whether there is an adequate level of oil in the oil pan 14 and, if so, to determine the viscosity of that oil. Therefore at step 92, the controller checks whether the timer's value ($\Delta T$) is less than a period of time $T_{AIR}$ which indicates that air is present in the oil sensor chamber 40. As noted previously, the length of time $\Delta T$ between when the voltage was initially applied to the electromagnetic coil 32, at which current began to flow, and the cusp 58 in the current waveform varies depending upon the viscosity of the fluid (oil or air) within the sensor chamber 40. Because oil is more viscous than air, its presence within the sensor chamber provides a greater resistance to motion of the plate causing a longer time interval $\Delta T$. Therefore, if the timer's measurement of $\Delta T$ is less than $T_{AIR}$, air is present in the sensor chamber 40 and the amount of oil in the oil pan 14 is below a desired level. Conversely, if the timer's measurement of $\Delta T$ is greater than $T_{AIR}$ then there is an adequate level of oil, because oil is present in the sensor chamber 40. The value of $T_{AIR}$ is a function of the particular design of the oil sensor 16 and is determined empirically.

If at step 92, the timer's measurement of time interval $\Delta T$ is less than the threshold value $T_{AIR}$, the process 60 provides an indication of a low oil level at step 94. The controller 53 sends that indication to via a communication link 55 to the instrument panel for the motor vehicle in which the engine 10 is located and activates the indicator 56.

Otherwise, when at step 92, the timer's measurement of $\Delta T$ is found greater the threshold $T_{AIR}$, as occurs when there is a desirable amount of oil, the process advances to step 96. At this point, any low oil indication that might have been set previously now is reset, as occurs after additional oil was added to the engine. Then the time interval $\Delta T$ is employed to determine the viscosity of the oil. The duration of time interval $\Delta T$ is directly related to the viscosity of the oil, i.e. the greater the viscosity, the longer the period $\Delta T$. The measurement of the time interval $\Delta T$ is used to address a lookup table stored in the memory of the controller 53 with the output of the lookup table being the viscosity value for the oil. That viscosity value can be displayed on the indicator 56. In addition the controller can compare the viscosity value from the lookup table to the known proper oil viscosity for the engine and when an improper viscosity is found a warning indication is provided via indicator 56 and the instrument panel of the motor vehicle.

After the oil detecting system 50 determines that the oil level is unacceptably low for proper engine operation, the system also can detect when oil has been added to an acceptable level. When the oil level in the oil pan 14 drops below the oil sensor 16, the oil drains from the sensor chamber 40 through the first aperture 47 at the bottom of the sensor housing 22. At that time, air enters the sensor chamber. Adding oil brings the level above the sensor 16, but does not immediately fill the sensor chamber 40 with oil because air is trapped therein preventing entry of oil. As a consequence, after a low oil indication has been given by the controller 53, the sensor 16 preferably is cycled by repeatedly energizing and de-energizing the solenoid's electromagnetic coil 32 to move the detector member 41 back and forth several times. This action to opens the second aperture 48, allowing the air to escape from the sensor chamber 40 and be replaced with oil, if the pan was refilled. If the oil pan 14 was not refilled, air will remain in the sensor chamber 40. At the end of the recycling when the sensor chamber 40 is filled with oil, the oil analysis process 60 determines that fact at step 92 as explained above and the previous low oil indication is reset at step 96.

The present oil sensor and signal processing also can be used to indicate when the engine oil has been changed. Many motor vehicles illuminate a light on the instrument panel when the oil should be changed. Presently a service technician must manually reset that light, the process for doing so differs with each make of motor vehicle. A determination by the present oil analysis process 60 that the oil has been changed can be used to turn off that light automatically. When oil is drained from the oil pan 14, the oil also drains from the sensor chamber 40 and is replaced by air. Refilling the oil pan 14 does not immediately fill the sensor chamber 40 with oil because the air is trapped therein preventing the entry of oil. Therefore while the change oil indicator light is illuminated, the sensor 16 is cycled by repeatedly energizing and de-energizing the solenoid's electromagnetic coil 32 to move the detector member 41 back and forth several times to open the second aperture 48 to allow the air to escape from the sensor chamber 40 and be replaced with oil, if the pan was refilled. During this cycling of the sensor solenoid 30 after an oil change, the controller 53 observes the time interval $\Delta T$ between the inception of the electric current and the cusp 58 getting significantly longer within five to seven cycles, due to the air being replaced by oil. In response to that observation, the controller 53 determines that the oil had been drained from the oil pan 14 and replaced. In response an indication that the oil has been changed is send via the communication link 55 to the controller that governs illumination of the oil change light on the instrument panel.

The foregoing description was primarily directed to a preferred embodiment of the invention. Although some attention was given to various alternatives within the scope of the invention, it is anticipated that one skilled in the art will likely realize additional alternatives that are now apparent from disclosure of embodiments of the invention. Accordingly, the scope of the invention should be determined from the following claims and not limited by the above disclosure.

The invention claimed is:

1. A system for detecting a characteristic of oil in a reservoir, said system comprising:
a sensor, at least partially located in the reservoir, and comprising a chamber for receiving oil from the reservoir, a detector member movably received in the chamber, and an electromagnetic coil application of a voltage across which causes movement of the detector member, the sensor further comprising a first aperture through which oil can drain by gravity from the chamber into the reservoir, and a second aperture between the chamber and the reservoir, the second aperture is opened and closed by movement of the detector member, wherein presence and absence of oil in the chamber affects the movement of the detector member which thereby alters a waveform of electric current flowing through the electromagnetic coil.

2. The system as recited in claim 1 further comprising a control circuit that periodically measures the electric current flowing through the electromagnetic coil to produce a series of electric current values, and responds to the series of electric current values by determining an amount of time that the detector member moves a predefined distance in the chamber.

3. The system as recited in claim 2 wherein the amount of time is determined by measuring a time interval between initial application of the voltage and a feature in the waveform of the electric current.

4. The system as recited in claim 2 wherein the amount of time is determined by measuring a time interval between initial application of the voltage and a change in the waveform of the electric current from a decreasing current segment to an increasing current segment.

5. The system as recited in claim 1 further comprising a control circuit that responds to the waveform of the electric current by determining whether there is at least a predefined amount of oil in the reservoir.

6. The system as recited in claim 2 wherein the oil has a viscosity and further comprising a control circuit that responds to the waveform of the electric current by determining the viscosity.

7. The system as recited in claim 1 further comprising a control circuit that responds to the waveform of the electric current by indicating that the oil in the chamber has been changed.

8. The system as recited in claim 1 wherein sensor further comprises a spring that biases the detector member away from the electromagnetic coil.

9. The system as recited in claim 1 further comprising a first pole piece located within the electromagnetic coil, wherein a first working gap is formed between the first pole piece and the detector member; and a second pole piece extending around the electromagnetic coil, wherein a second working gap is formed between the second pole piece and the detector member.

10. The system as recited in claim 1 wherein detector member is a disk-shaped plate.

11. The system as recited in claim 10 wherein the disk-shaped plate slides along a guide pin.

12. A system for detecting a characteristic of oil in a reservoir, said system comprising:
a sensor comprising a chamber for receiving oil from the reservoir, an electromagnetic coil, a detector member that moves within the chamber in response to application of electric current to the electromagnetic coil, wherein a portion of the chamber is formed outside the electromagnetic coil between the detector member and the electromagnetic coil, and wherein presence and absence of oil in the chamber affects the movement of the detector member which thereby alters a waveform of the electric current flowing through the electromagnetic coil;
a coil driver that produces an electric voltage which is applied across the electromagnetic coil;

a current sensor that measures the electric current flowing through the electromagnetic coil; and a controller coupled to the current sensor and responds to measurement of the electric current by determining an amount of time that the detector member moves between first and second positions in the chamber, and wherein the controller determines the characteristic of the oil in the reservoir based on the amount of time.

13. The system as recited in claim 12 wherein the amount of time is determined by measuring a time interval between initial application of the voltage and a cusp in the waveform of the electric current.

14. The system as recited in claim 12 wherein the amount of time is determined by measuring a time interval between initial application of the voltage and a change in the waveform of the electric current from a decreasing current segment to an increasing current segment.

15. The system as recited in claim 12 wherein the controller responds to the amount of time by determining whether there is at least a predefined amount of oil in the reservoir.

16. The system as recited in claim 12 wherein the oil has a viscosity and the controller responds to the amount of time by determining the viscosity.

17. The system as recited in claim 12 wherein the controller responds to the amount of time by indicating that the oil in the chamber has been changed.

18. The system as recited in claim 12 wherein sensor further comprises a spring that biases the detector member away from the electromagnetic coil.

19. The system as recited in claim 12 wherein sensor comprises a first aperture through which oil can drain by gravity from the chamber into the reservoir; and a second aperture between the chamber and the reservoir, wherein second aperture is opened and closed by movement of the detector member.

20. The system as recited in claim 12 further comprising a first pole piece located within the electromagnetic coil, wherein a first working gap is formed between the first pole piece and the detector member; and a second pole piece extending around the electromagnetic coil, wherein a second working gap is formed between the second pole piece and the detector member, wherein both the first and second working gaps change in size when the detector member moves.

21. The system as recited in claim 12 wherein detector member is a disk-shaped plate.

22. The system as recited in claim 21 wherein the disk-shaped plate slides along a guide pin.

23. A system for detecting a characteristic of oil in a reservoir, said system comprising:

a sensor, at least partially located in the reservoir, and comprising a chamber for receiving oil from the reservoir, a detector member movably received in the chamber, and an electromagnetic coil application of electric current to which causes movement of the detector member, a first pole piece located within the electromagnetic coil, wherein a first working gap is formed between the first pole piece and the detector member, and a second pole piece extending around the electromagnetic coil, wherein a second working gap is formed between the second pole piece and the detector member, and both the first and second working gaps change in size when the detector member moves; and wherein presence and absence of oil in the chamber affects the movement of the detector member which thereby alters a waveform of the electric current.

24. The system as recited in claim 23 wherein the sensor further comprises a first aperture through which oil can drain by gravity from the chamber into the reservoir, and a second aperture between the chamber and the reservoir, the second aperture is opened and closed by movement of the detector member.

* * * * *